United States Patent [19]

Idelson

[11] 4,336,405

[45] Jun. 22, 1982

[54] SILVER HALIDE DEVELOPING AGENTS

[75] Inventor: Elbert M. Idelson, West Newton, Mass.

[73] Assignee: Polaroid Corporation, Cambridge, Mass.

[21] Appl. No.: 168,641

[22] Filed: Jul. 11, 1980

Related U.S. Application Data

[63] Continuation-in-part of Ser. No. 89,556, Oct. 29, 1979, abandoned, which is a continuation-in-part of Ser. No. 1,447, Jan. 8, 1979, abandoned.

[51] Int. Cl.$^3$ ........................ C07C 101/72; G03C 5/30

[52] U.S. Cl. .................................... 562/448; 562/444; 562/426; 546/227; 260/501.12; 548/533; 430/484

[58] Field of Search ................ 562/448, 444; 546/227; 260/501.12, 326.46

[56] References Cited

U.S. PATENT DOCUMENTS

| | | | |
|---|---|---|---|
| 3,133,816 | 5/1964 | Ben-Ezra | 260/501.13 |
| 3,265,724 | 8/1966 | Zienty | 562/444 |
| 3,453,107 | 7/1969 | Idelson . | |
| 3,463,812 | 8/1969 | Thunberg et al. . | |
| 3,563,739 | 2/1971 | Idelson . | |
| 3,629,336 | 12/1971 | Idelson . | |
| 3,679,728 | 7/1972 | Morgan et al. | 562/444 |
| 3,697,271 | 10/1972 | Timson . | |
| 3,789,062 | 1/1974 | Idelson . | |
| 4,116,991 | 9/1978 | Leneuf . | |

OTHER PUBLICATIONS

Khramor et al., Chem. Absts., 82, 35411(e), 1975.

Khramor et al., Chem. Absts., 80, 103334(t), 1974.

*Primary Examiner*—G. T. Breitenstein

*Attorney, Agent, or Firm*—Gaetano D. Maccarone

[57] ABSTRACT

There are described novel compounds which include a silver halide developing function, a colorless ligand which is a radical of an iminodiacetic acid and a radical containing an onium group. The compounds are useful in photography as silver halide developing agents and also may be complexed with metals to form dye developers.

2 Claims, No Drawings

SILVER HALIDE DEVELOPING AGENTS

CROSS-REFERENCE TO RELATED APPLICATIONS

This application is a continuation-in-part of prior copending application Ser. No. 089,556, filed Oct. 29, 1979, now abondoned, which is a continuation-in-part of prior copending application Ser. No. 001,447, filed Jan. 8, 1979, now abandoned.

BACKGROUND OF THE INVENTION

This invention relates to novel compounds and more particularly to a to a novel class of ligands which include a silver halide developing function.

As is well known in the art, ligands are coordinating agents which will form a coordination complex with a metal. Those atoms of the ligand which are linked directly to the metal cation are called coordinating or donor atoms and each metal ion requires several of these atoms to make up its coordination number. According to the number of coordinating atoms which it contains, the complex-forming agent or ligand is said to be uni-dentate (one "tooth") or multi-dentate, e.g., bidendate, tri-dentate, etc. Ligands are further classified as organic or inorganic. In organic ligands, the coordination atoms (generally O, N or S) are attached to the carbon skeleton of an organic molecule. One particularly useful application of such compounds is in the field of dye technology to form a stable metal-dye complex, also commonly referred to as a metallized dye.

Ligands which have integrated therewith a silver halide developing function are known. However, as the art of photography advances, new materials are continually sought because of different performance requirements which are imposed. The present application relates to a novel class of materials which include a ligand and a silver halide developing function and their use in photographic processes, and the preparation of other photographic materials and products.

SUMMARY OF THE INVENTION

It is therefore the object of this invention to provide novel compounds which are useful in photography.

It is another object of the invention to provide photographic products and processes utilizing the novel compounds.

It is a further object to provide compounds which include a silver halide developing function and a colorless ligand which is an iminodiacetic acid.

Still another object is to provide compounds which include a radical containing an onium group.

A further object is to provide compounds which are useful in the preparation of dye developers for use in photography.

BRIEF SUMMARY OF THE INVENTION

These and other objects and advantages are accomplished in accordance with the invention by providing novel compounds which include a silver halide developing function, a colorless ligand which is a radical of an iminodiacetic acid and a radical containing an onium group. The novel compounds of the invention are within one of the following formulas

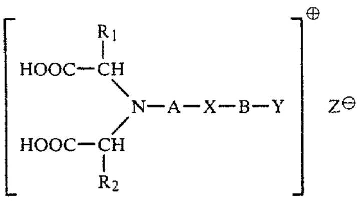

FORMULA A

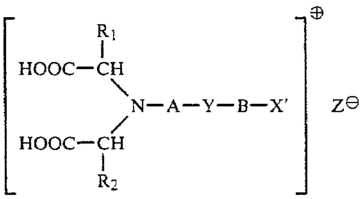

FORMULA B

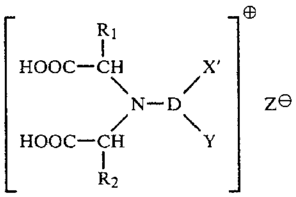

FORMULA C wherein $R_1$ and $R_2$ may be H or when taken together represent the carbon atoms necessary to complete a five or six member heterocyclic moiety; X and X′ are each radicals containing an onium group; Y is a silver halide developing substituent; A and B are each alkylene having from 1 to 6 carbon atoms with the proviso that the sum of the carbon atoms of A and B is not greater than 8; D is a saturated aliphatic radical having up to 6 carbon atoms; and Z is an anion.

It should be noted that both A and B may be either straight or branched chain alkylene groups.

For the present invention, a silver halide developing substituent (Y) is one containing a phenyl or naphthyl nucleus containing at least a hydroxy and/or amino substituent ortho or para to another such substituent. Silver halide developing moieties of this type are well known to the art as evidenced, for example by Neblette's handbook of Photography and Repropgraphy, 7th Edition, published by Van Nostrand Reinhold Company, Inc. (1977), pp. 115–118. A preferred group of developing substituents are the hydroquinonyls, including substituted derivatives thereof such as alkyl, phenyl and/or alkoxy substituted derivatives of hydroquinone.

The radicals containing an onium group (X and X′), may be any such as, for example, ammonium, phosphonium or sulfonium which do not impair photographic processing, i.e., impair the functionality of the compound as a silver halide developer agent. One class of onium radicals which may be used is represented by the formula:

$$N^{\oplus}R_3R_4R_5R_6$$

wherein $R_3$ is alkylene having from two to eight carbon atoms and $R_4$, $R_5$ and $R_6$ may be H or alkyl, preferably alkyl having from one to six carbon atoms. It will be apparent that the onium group is connected to the ligand through one of the R groups.

As noted, the ligand is a radical of an iminodiacetic acid which is represented by the structural formula:

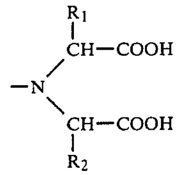

wherein $R_1$ and $R_2$ may be H or when taken together represent the carbon atoms necessary to complete a five or six member heterocyclic moiety. A preferred ligand of the latter type is a radical of an iminodiacetic acid which is represented by the structural formula:

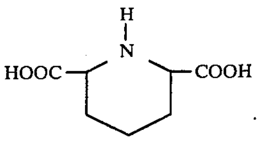

The anion, Z, may be any suitable anion such as, for example, chloride, sulfate, tosylate, etc.

DESCRIPTION OF THE PREFERRED EMBODIMENTS

Specific preferred compounds of the present invention are represented by the following formulas:

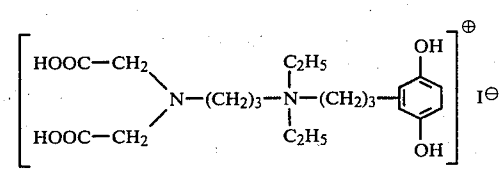

(I)

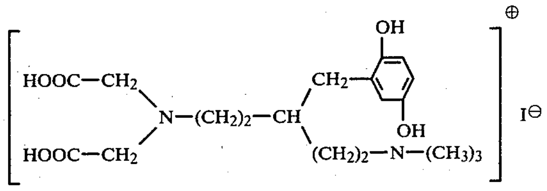

(II)

The preparation of the novel ligands of the invention can be carried out by reactions which are known in the art and therefore extensive discussion of techniques for preparation is not required here. Generally, the ligands can be prepared by reacting amine compounds which have a blocked hydroquinone moiety with chloroacetic acid in the presence of a base such as barium hydroxide and subsequently removing the blocking groups from the hydroquinone moiety. For example, compound II can be prepared by reacting the appropriate aminoalcohol containing a conveniently blocked hydroquinone moiety with chloroacetic acid to convert the amino group to the iminodiacetic acid moiety followed by converting the alcoholic —OH group to the onium containing radical by first forming a tosylate ester group by reaction with tosyl chloride, subsequently reacting it with trimethylamine and removing the blocking groups from the hydroquinone moiety.

The invention will now be further described in detail with respect to specific preferred embodiments thereof by way of examples, it being understood that these are intended to be illustrative only and the invention is not intended to be limited to the materials, conditions, process parameters, etc. which are recited therein. All parts and percentages are by weight unless otherwise specified.

EXAMPLE I

PREPARATION OF COMPOUND I

N-(triphenylmethyl)-3N',N'-dimethylaminopropylamine was formed by initially adding 55.9 g (0.2 mole) of triphenylmethyl chloride in one portion to a stirred solution of 26 g (0.2 mole) of 3-diethylaminopropylamine and 20 g (0.2 mole) of triethylamine in methylene chloride at room temperature under nitrogen. The reaction immediately warmed to 40° C. A solid began to form after two hours. The reaction mixture was stirred for twelve hours. The solution was filtered from triethylamine hydrochloride. The filtrate was washed with two 100 ml volumes of water and 100 ml of saturated salt solution and then dried over sodium sulfate. The solution was filtered and evaporated to dryness to yield 74.5 g of a light yellow oil.

A mixture of 7.45 g (0.02 mole) of the previous product and 10.05 g (0.02 mole) of 3-(2',5'-dibenzyloxyphenyl) propyl-1-tosylate was heated on a steam bath for 18 hours, cooled to room temperature and dissolved in a minimum amount of chloroform. The solution was diluted with ether and cooled in ice. Solvents were decanted from the precipitated oil, the oil rinsed twice with ether and dried under high vacuum to give 15 g of a white solid.

To a solution of 14 g (0.016 mole) of the white solid in 25 ml of acetone, there was added a solution of 7.2 g (0.048 mole) of sodium iodide in 40 ml of acetone. The mixture stood for twenty minutes with occasional agitation. The precipitate was then filtered and washed with acetone. The combined acetone filtrates were evaporated to dryness under vacuum. The residue was dissolved in chloroform and the chloroform solution washed twice with water, dried over anhydrous sodium sulfate and evaporated under vacuum to yield an oil. The oil yielded 12.6 g of a solid under high vacuum.

A solution of 52 g (0.0626 mole) of the previous product in 75 ml of 1 N ethanolic hydrogen chloride was refluxed under nitrogen for one hour. The reaction mixture was cooled and diluted with ether. Solvents were decanted from the precipitated oil which was then rinsed twice with ether and dried under high vacuum. The residue was dissolved in methanol, a little water and Norit added and then warmed on a steam bath. After filtering, the filtrate was evaporated under vacuum to yield 26 g. of a hygroscopic solid.

To a solution of 26 g (0.0416 mole) of the previous product and 7.87 g (0.0832 mole) of chloroacetic acid in 250 ml of water there were added 32.8 g (0.104 mole) of barium hydroxide octahydrate. The mixture was stirred under nitrogen at 50° C. for 22 hours. The reaction mixture was cooled in an ice bath and the precipitate collected by filtration, washed with cold water and dried to give 24 g of white solid.

A suspension of 24 g (0.02855 mole) of the previous product in 200 ml of water was heated on a steam bath. Then a solution of 2.8 g of conc. sulfuric acid in 15 ml of water was added dropwise and with stirring over a half hour period. When almost all of the sulfuric acid solution had been added (pH 3–4) a gummy precipitate had formed. The reaction mixture was cooled to room temperature, the aqueous solvents decanted off and the residue triturated with methanol and filtered from barium sulfate. The methanol filtrate was evaporated under vacuum to an oil which was dried overnight under vacuum to give 17 g of a hygroscopic solid.

A solution of 13 g (0.01845 mole) of the previous product in 200 ml of methylene chloride was cooled to −78° C. and, with stirring, hydrogen bromide gas was bubbled in for fifteen minutes. The cooling bath was removed then and stirring with hydrogen bromide gas bubbling in was continued for an additional hour while the reaction mixture was warming slowly. The precipitate was filtered under nitrogen, washed well with methylene chloride and dried under vacuum, over sodium hydroxide, to give 10 g of a light yellow solid (compound I). The NMR spectrum of the yellow solid was in agreement with the structure of compound I.

Although the invention has been described in detail with respect to various embodiments thereof, these are intended to be illustrative only and not limiting of the invention but rather those skilled in the art will recognize that modifications and variations may be made therein which are within the spirit of the invention and the scope of the appended claims.

What is claimed is:

1. A compound which is represented by the formula

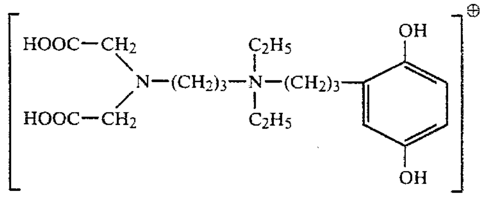

wherein Z is an anion.

2. A compound which is represented by a formula selected from the group consisting of

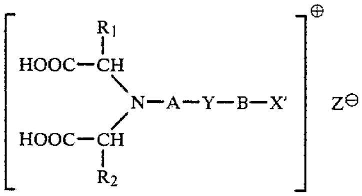

and

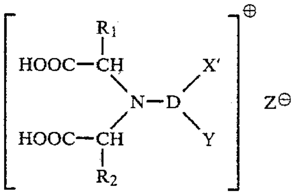

wherein $R_1$ and $R_2$ are each H or when taken together represent the carbon atoms necessary to complete a five or six member heterocyclic moiety; X' is N $R_3R_4R_5R_6$; $R_3$ is alkylene having from 2 to 8 carbon atoms; $R_4$, $R_5$ and $R_6$ each is H or alkyl having from 1 to 6 carbon atoms; Y is a hydroquinonyl group; A and B are each alkylene having from 1 to 6 carbon atoms provided that the sum of the carbon atoms of A and B is not greater than 8; D is a saturated aliphatic radical having up to 6 carbon atoms; and Z is an anion.

* * * * *